(12) United States Patent
Butler et al.

(10) Patent No.: US 7,495,139 B2
(45) Date of Patent: Feb. 24, 2009

(54) USE OF MODIFIED ZEOLITE CATALYSTS IN ALKYLATION SYSTEMS

(75) Inventors: James R. Butler, League City, TX (US); Kevin P. Kelly, Friendswood, TX (US)

(73) Assignee: Fina Technology, Inc., Houston, TX (US)

( * ) Notice: Subject to any disclaimer, the term of this patent is extended or adjusted under 35 U.S.C. 154(b) by 335 days.

(21) Appl. No.: 11/326,658

(22) Filed: Jan. 7, 2006

(65) Prior Publication Data
US 2007/0161836 A1    Jul. 12, 2007

(51) Int. Cl.
*C07C 2/66* (2006.01)

(52) U.S. Cl. ........................................ 585/448; 585/467

(58) Field of Classification Search ................. 585/448, 585/467
See application file for complete search history.

(56) References Cited

U.S. PATENT DOCUMENTS

| | | |
|---|---|---|
| 3,308,069 A | 3/1967 | Wadlinger et al. |
| 4,185,040 A | 1/1980 | Ward et al. |
| 4,642,226 A | 2/1987 | Calvert et al. |
| 4,721,824 A | 1/1988 | McWilliams |
| 6,933,418 B2 | 8/2005 | Kelly et al. |
| 2004/0059167 A1 | 3/2004 | Clark |

*Primary Examiner*—Thuan Dinh Dang
(74) *Attorney, Agent, or Firm*—Tenley R. Krueger

(57) ABSTRACT

Alkylation systems and methods are described herein and generally include contacting an alkyl aromatic hydrocarbon with a cerium promoted zeolite catalyst and then contacting the alkyl aromatic hydrocarbon with an alkylation catalyst to form a second aromatic hydrocarbon.

8 Claims, 1 Drawing Sheet

USE OF MODIFIED ZEOLITE CATALYSTS IN ALKYLATION SYSTEMS

FIELD

Embodiments of the present invention generally relate to alkylation of aromatic compounds. In particular, embodiments of the invention generally relate to modification of zeolite catalysts for use in alkylation systems.

BACKGROUND

Alkylation reactions generally involve contacting a first aromatic compound with an alkylation catalyst to form a second aromatic compound. Unfortunately, alkylation catalyst systems generally experience deactivation requiring either regeneration or replacement, some of the deactivation resulting from poisons present in the input stream to the alkylation system. Therefore, a need exists to develop an alkylation system that is capable of reducing alkylation catalyst deactivation.

SUMMARY

Embodiments of the present invention include an alkylation system. The alkylation system generally includes a first alkylation system adapted to receive a first input stream and contact the first input stream with a cerium promoted zeolite catalyst disposed therein to form a first output stream. The first input stream generally includes an alkyl aromatic hydrocarbon. The alkylation system further includes a second alkylation system adapted to receive a second input stream and contact the second input stream with an alkylation catalyst disposed therein to form a second output stream. The second input stream generally includes the first output stream.

Embodiments of the invention further include an alkylation method including contacting an alkyl aromatic hydrocarbon with a cerium promoted zeolite catalyst and then contacting the alkyl aromatic hydrocarbon with an alkylation catalyst to form a second aromatic hydrocarbon.

Embodiments of the invention further include a method of minimizing alkylation catalyst regeneration. The method generally includes substantially continuously feeding an input stream to an alkylation system, contacting the input stream with an alkylation catalyst to form an output stream and removing the output stream from the alkylation system over a period of time substantially equal to the catalyst life. The alkylation input stream generally includes a first aromatic compound and an alkylating agent and the alkylation output generally includes a second aromatic compound. The method further includes contacting the input stream with a cerium promoted zeolite catalyst prior to feeding the input stream to the alkylation system, wherein the catalyst life is longer than the catalyst life in the absence of contact with the cerium promoted zeolite catalyst.

DETAILED DESCRIPTION

Introduction and Definitions

Figure 1:
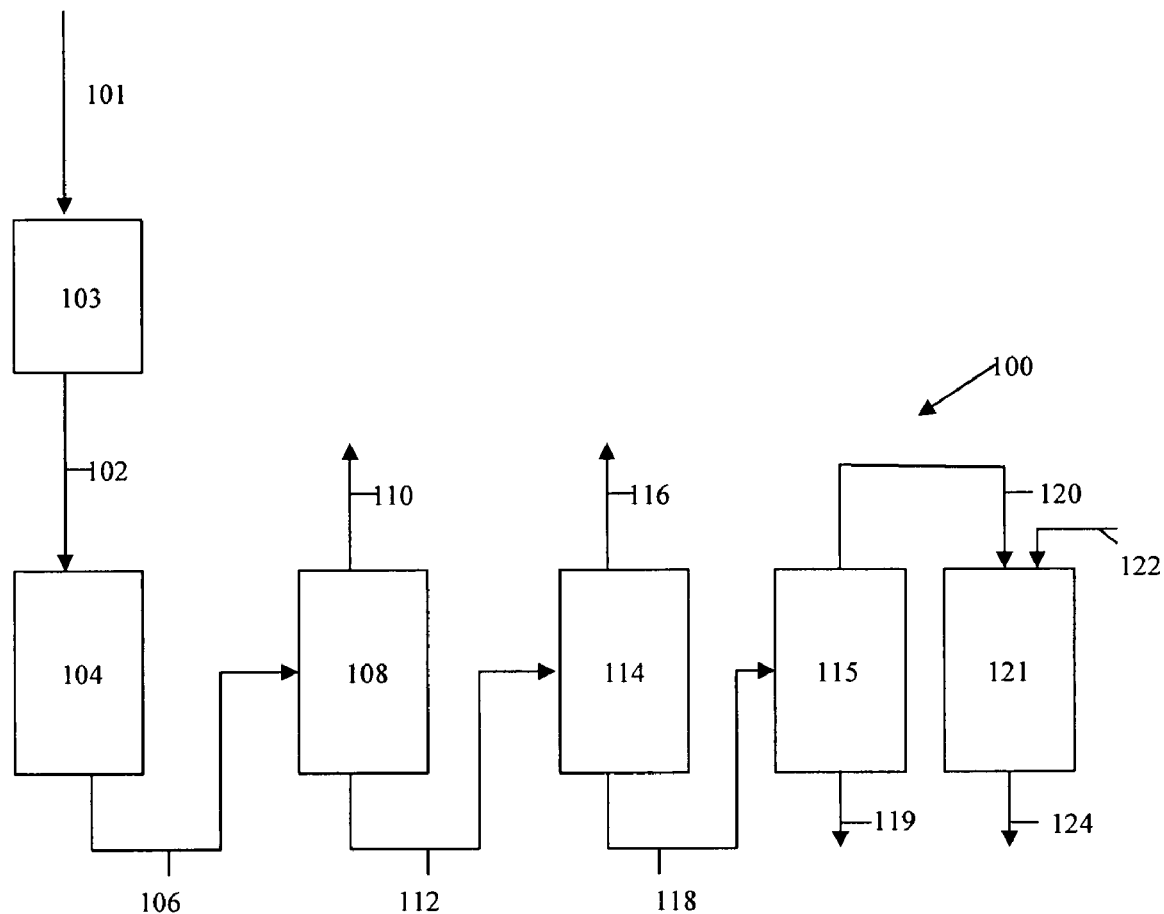
FIG. 1 illustrates an alkylation/transalkylation process.

A detailed description will now be provided. Each of the appended claims defines a separate invention, which for infringement purposes is recognized as including equivalents to the various elements or limitations specified in the claims. Depending on the context, all references below to the "invention" may in some cases refer to certain specific embodiments only. In other cases it will be recognized that references to the "invention" will refer to subject matter recited in one or more, but not necessarily all, of the claims. Each of the inventions will now be described in greater detail below, including specific embodiments, versions and examples, but the inventions are not limited to these embodiments, versions or examples, which are included to enable a person having ordinary skill in the art to make and use the inventions, when the information in this patent is combined with available information and technology.

Various terms as used herein are shown below. To the extent a term used in a claim is not defined below, it should be given the broadest definition persons in the pertinent art have given that term as reflected in printed publications and issued patents. Further, unless otherwise specified, all compounds described herein may be substituted or unsubstituted and the listing of compounds includes derivatives thereof.

The term "activity" refers to the weight of product produced per weight of the catalyst used in a process per hour of reaction at a standard set of conditions (e.g., grams product/gram catalyst/hr).

The term "conversion" refers to the percentage of input converted.

The term "deactivated catalyst" refers to a catalyst that has lost enough catalyst activity to no longer be efficient in a specified process. The term "substantially equal to the catalyst life" refers to a time period that is approximately equal to the time a catalyst is exposed to a reaction environment to the time that the catalyst becomes deactivated.

The term "recycle" refers to returning an output of a system as input to either that same system or another system within a process. The output may be recycled to the system in any manner known to one skilled in the art, for example, by combining the output with the input stream or by directly feeding the output into the system. In addition, multiple input streams may be fed to a system in any manner known to one skilled in the art.

The term "regenerated catalyst" refers to a catalyst that has regained enough activity to be efficient in a specified process. Such efficiency is determined by individual process parameters.

The term "regeneration" refers to a process for renewing catalyst activity and/or making a catalyst reusable after its activity has reached an unacceptable level. Examples of such regeneration may include passing steam over a catalyst bed or burning off carbon residue, for example.

Embodiments of the invention generally relate an alkylation system adapted to minimize alkylation catalyst deactivation.

FIG. 1 illustrates a schematic block diagram of an embodiment of an alkylation/transalkylation process 100. The process 100 generally includes supplying an input stream 102 (e.g., a first input stream) to an alkylation system 104 (e.g., a first alkylation system.) The alkylation system 104 is generally adapted to contact the input stream 102 with an alkylation catalyst to form an alkylation output stream 106 (e.g., a first output stream).

At least a portion of the alkylation output stream 106 passes to a first separation system 108. An overhead fraction is generally recovered from the first separation system 108 via line 110 while at least a portion of the bottoms fraction is passed via line 112 to a second separation system 114.

An overhead fraction is generally recovered from the second separation system 114 via line 116 while at least a portion of a bottoms fraction is passed via line 118 to a third separation system 115. A bottoms fraction is generally recovered from the third separation system 115 via line 119 while at least a portion of an overhead fraction is passed via line 120 to a transalkylation system 121. In addition to the overhead fraction 120, an additional input, such as additional aromatic compound, is generally supplied to the transalkylation system 121 via line 122 and contacts the transalkyation catalyst, forming a transalkylation output 124.

Although not shown herein, the process stream flow may be modified based on unit optimization so long as the modification complies with the spirit of the invention, as defined by the claims. For example, at least a portion of any overhead fraction may be recycled as input to any other system within the process. Also, additional process equipment, such as heat exchangers, may be employed throughout the processes described herein and such placement is generally known to one skilled in the art.

Further, while described below in terms of primary components, the streams indicated below may include any additional components as known to one skilled in the art.

The input stream 102 generally includes an aromatic compound and an alkylating agent. The aromatic compound may include substituted or unsubstituted aromatic compounds. If present, the substituents on the aromatic compounds may be independently selected from alkyl, aryl, alkaryl, alkoxy, aryloxy, cycloalkyl, halide and/or other groups that do not interfere with the alkylation reaction, for example. Examples of substituted aromatic compounds generally include toluene, xylene, isopropylbenzene, normal propylbenzene, alpha-methylnaphthalene, ethylbenzene, mesitylene, durene, cymene, butylbenzene, pseudocumene, o-diethylbenzene, m-diethylbenzene, p-diethylbenzene, isoamylbenzene, isohexylbenzene, pentaethylbenzene, pentamethylbenzene, 1,2,3,4-tetraethylbenzene, 1,2,3,5-tetramethylbenzene, 1,2,4-triethylbenzene, 1,2,3-trimethylbenzene, m-butyltoluene, p-butyltoluene, 3,5-diethyltoluene, o-ethyltoluene, p-ethyltoluene, m-propyltoluene, 4-ethyl-m-xylene, dimethylnaphthalenes, ethylnaphthalene, 2,3-dimethylanthracene, 9-ethylanthracene, 2-methylanthracene, o-methylanthracene, 9,10-dimethylphenanthrene and 3-methyl-phenanthrene. Further examples of aromatic compounds include hexylbenzene, nonylbenzene, dodecylbenzene, pentadecylbenzene, hexyltoluene, nonyltoluene, dodecyltoluene and pentadecytoluene. In another embodiment, the aromatic compound includes hydrocarbons, such as benzene, naphthalene, anthracene, naphthacene, perylene, coronene and phenanthrene, for example.

The alkylating agent may include olefins (e.g., ethylene, propylene, butene and pentene), alcohols (e.g., methanol, ethanol, propanol, butanol and pentanol), aldehydes (e.g., formaldehyde, acetaldehyde, propionaldehyde, butyraldehyde and n-valeraldehyde) and/or alkyl halides (e.g., methyl chloride, ethyl chloride, propyl chloride, butyl chloride and pentyl chloride), for example. In one embodiment, the alkylating agent includes a mixture of light olefins, such as mixtures of ethylene, propylene, butene and/or pentenes, for example.

In addition to the aromatic compound and the alkylating agent, the input stream 102 may further include other compounds in minor amounts (e.g., sometimes referred to as poisons or inactive compounds,) such as $C_7$ aliphatic compounds and/or nonaromatic compounds, for example. In one embodiment, the input stream 102 includes less than about 3% of such compounds or less than about 1%, for example (e.g., about 100 ppb or less, or about 80 ppb or less or about 50 ppb or less.)

In one embodiment, the alkylation system 104 may include a plurality of multi-stage reaction vessels (not shown). In one embodiment, the plurality of multi-stage reaction vessels include a plurality of operably connected catalyst beds, such beds containing an alkylation catalyst (not shown.) Such reaction vessels are generally liquid or vapor phase reactors operated at reactor temperatures and pressures sufficient to maintain the alkylation reaction in the liquid phase, the vapor phase, the supercritical phase or combinations thereof, i.e., the phase of the aromatic compound, for example. Such temperatures and pressures are generally determined by individual process parameters.

The alkylation output 106 generally includes a second aromatic compound, for example. In one embodiment, the second aromatic compound includes ethylbenzene, for example.

The first separation system 108 may include any process or combination of processes known to one skilled in the art for the separation of aromatic compounds. For example, the first separation system 108 may include one or more distillation columns (not shown,) either in series or in parallel. The number of such columns may depend on the volume of the alkylation output 106 passing therethrough, for example.

The overhead fraction 110 from the first separation system 108 generally includes the first aromatic compound, such as benzene, for example.

The bottoms fraction 112 from the first separation system 108 generally includes the second aromatic compound, such as ethylbenzene, for example.

The second separation system 114 may include any process known to one skilled in the art, for example, one or more distillation columns (not shown), either in series or in parallel.

The overhead fraction 116 from the second separation system 114 generally includes the second aromatic compound, such as ethylbenzene, which may be recovered and used for any suitable purpose, such as the production of styrene, for example.

The bottoms fraction 118 from the second separation system 114 generally includes heavier aromatic compounds, such as polyethylbenzene, cumene and/or butylbenzene, for example.

The third separation system 115 generally includes any process known to one skilled in the art, for example, one or more distillation columns (not shown), either in series or in parallel.

In a specific embodiment, the overhead fraction 120 from the third separation system 115 may include diethylbenzene and liquid phase triethylbenzene, for example. The bottoms fraction 119 (e.g., heavies) may be recovered from the third separation system 115 for further processing and recovery (not shown).

The transalkylation system 121 generally includes one or more reaction vessels having a transalkylation catalyst disposed therein. The reaction vessels may include any reaction vessel, combination of reaction vessels and/or number of reaction vessels (either in parallel or in series) known to one skilled in the art.

The transalkylation output 124 generally includes the second aromatic compound, for example.

In one embodiment, the transalkylation system 121 is operated under liquid phase conditions. For example, the transalkylation system 121 may be operated at a temperature of from about 65° C. to about 290° C. and a pressure of about 700 psig or less. In another embodiment, the transalkylation system 121 is operated under vapor phase conditions, for example.

In a specific embodiment, the input stream 102 includes benzene and ethylene. The benzene may be supplied from a variety of sources, such as a fresh benzene source and/or a variety of recycle sources. As used herein, the term "fresh benzene source" refers to a source including at least about 95 wt. % benzene, at least about 98 wt. % benzene or at least about 99 wt. % benzene, for example. As used herein, the term "recycle" refers to an output of a system, such as an alkylation system and/or a dehydrogenation system, which is then returned as input to either that same system or another system the same process. In one embodiment, the molar ratio of benzene to ethylene in the input stream 102 may be from about 1:1 to about 30:1, or from about 1:1 to about 20:1 or from about 5:1 to about 15:1, for example.

In a specific embodiment, benzene is recovered through line 110 and recycled (not shown) as input to the alkylation system 104, while ethylbenzene and/or polyalkylated benzenes are recovered via line 112.

As previously discussed, the alkylation system 104 generally includes an alkylation catalyst. The input stream 102, e.g., benzene/ethylene, contacts the alkylation catalyst during the alkylation reaction to form the alkylation output 106, e.g., ethylbenzene.

Unfortunately, alkylation catalyst systems generally experience deactivation requiring either regeneration or replacement. The deactivation results from a number of factors. One of those factors is that poisons present in the input stream 102, such as nitrogen, sulfur and/or oxygen containing impurities, either naturally occurring or a result of a prior process, may reduce the activity of the alkylation catalyst.

Therefore, the alkylation/transalkylation system 100 may further include a preliminary alkylation system 103. The preliminary alkylation system 103 may be maintained at ambient or up to alkylation conditions, for example. The preliminary alkylation input stream 101 may be passed through the preliminary alkylation system 103 prior to entry into the alkylation system 104 to reduce the level of poisons in the input stream 102, for example. In one embodiment, the level of poisons is reduced by at least 10%, or at least 20% or at least 30% or at least 40% or at least 50%, for example. For example, the preliminary alkylation system 103 may be used as a sacrificial system, thereby reducing the amount of poisons contacting the alkylation catalyst in the alkylation system 104, thereby minimizing the amount of regeneration of such catalyst.

The preliminary alkylation system 103 may be operated under liquid phase and/or vapor phase conditions. For example, the preliminary alkylation system 103 may be operated at a temperature of from about 20° C. to about 270° C. and a pressure of from about 675 kPa to about 8300 kPa.

The preliminary alkylation system 103 generally includes a preliminary catalyst (not shown) disposed therein.

The alkylation catalyst, transalkylation catalyst and/or the preliminary catalyst may be the same or different. In general, such catalysts are selected from molecular sieve catalysts, such as zeolite Y or zeolite beta catalysts, for example.

As a result of the level of poisons present in the preliminary alkylation input 101, the preliminary catalyst in the preliminary alkylation system 103 may be deactivated rapidly, requiring frequent regeneration and/or replacement. For example, the preliminary catalyst may experience deactivation more rapidly than the alkylation catalyst (e.g., twice as often or 1.5 times as often.)

Therefore, embodiments of the invention generally utilize a cerium promoted zeolite catalyst in the preliminary alkylation system 103. In addition, it is contemplated that the alkylation and/or transalkylation catalyst may also utilize such cerium promoted catalyst.

In one embodiment, the cerium promoted zeolite catalyst is a cerium promoted zeolite beta catalyst. The cerium promoted zeolite beta (e.g., cerium beta) catalyst may be formed from any zeolite catalyst known to one skilled in the art. For example, the cerium beta catalyst may include zeolite beta modified by the inclusion of cerium. Any method of modifying the zeolite beta catalyst with cerium may be used. For example, in one embodiment, the zeolite beta may be formed by mildly agitating a reaction mixture including an alkyl metal halide and an organic templating agent for a time sufficient to crystallize the reaction mixture and form the zeolite beta (e.g., from about 1 day to many months via hydrothermal digestion), for example. The alkyl metal halide may include silica, alumina, sodium or another alkyl metal oxide, for example. The hydrothermal digestion may occur at temperatures of from slightly below the boiling point of water at atmospheric pressure to about 170° C. at pressures equal to or greater than the vapor pressure of water at the temperature involved, for example.

The zeolite beta may have a silica to alumina molar ratio (expressed as $SiO_2/Al_2O_3$) of from about 10 to about 200 or about 20 to about 50, for example. In one embodiment, the zeolite beta may have a low sodium content, e.g., less than about 0.2 wt. % expressed as $Na_2O$, or less than about 0.02 wt. %, for example. The sodium content may be reduced by any method known to one skilled in the art, such as through ion exchange, for example. The formation of zeolite beta is further described in U.S. Pat. Nos. 3,308,069 and 4,642,226, which are incorporated by reference herein.

In another embodiment, it is contemplated that a cerium promoted zeolite Y catalyst may be used. It is further contemplated that the zeolite Y catalyst may be modified with cerium in the same manner as the modification of zeolite beta. The formation of Zeolite Y is described in U.S. Pat. No. 4,185,040, which is incorporated by reference herein.

Unexpectedly, it has been found that the cerium promoted zeolite catalyst can be regenerated to a level higher than that of previous zeolite catalysts utilized in the preliminary alkylation system 103. Such unexpected regeneration provides for increased catalyst activity and/or longer run times between regeneration and/or replacement of the catalyst.

In one embodiment, the zeolite catalyst is modified with a rare earth metal ion, such as lanthanum, cerium, neodymium or praseodymium, for example. As previously discussed, it has been discovered that cerium based zeolite catalyst demonstrate an unexpected improvement in activity and selectivity over lanthanum based zeolite catalyst systems. However, it is contemplated that the acidity of the rare earth metal ion based zeolite catalyst systems may be modified to enhance the activity and/or selectivity thereof. Such modification of the acidity may be accomplished through the processes described in J. Catal. 205, 58-66 (2002), which is incorporated by reference herein.

When regeneration of any catalyst within the system is desired, the regeneration procedure generally includes processing the deactivated catalyst at high temperatures, although the regeneration may include any regeneration procedure known to one skilled in the art.

Once a reactor is taken off-line, the catalyst disposed therein may be purged. Off-stream reactor purging may be performed by contacting the catalyst in the off-line reactor with a purging stream, which may include any suitable inert gas (e.g., nitrogen), for example. The off-stream reactor purging conditions are generally determined by individual process parameters and are generally known to one skilled in the art.

The catalyst may then undergo regeneration. The regeneration conditions may be any conditions that are effective for at least partially reactivating the catalyst and are generally known to one skilled in the art. For example, regeneration may include heating the alkylation catalyst to a temperature or a series of temperatures, such as a regeneration temperature of from about 50° C. to about 400° C. above the purging or alkylation reaction temperature, for example.

In one embodiment, the alkylation catalyst is heated to a first temperature (e.g., 700° F.) with a gas containing nitrogen and about. 2% oxygen, for example, for a time sufficient to provide an output stream having an oxygen content of about 0.5%. The alkylation catalyst may then be heated to a second temperature for a time sufficient to provide an output stream having an oxygen content of about 2.0%. The second temperature may be about 50° F. greater than the first temperature, for example. The second temperature is generally about 950° F. or less, for example. The catalyst may further be held at the second temperature for a period of time, or at a third temperature that is greater than the second temperature, for example.

Upon catalyst regeneration, the reactor is then ready to be placed on-line for continued production.

While the foregoing is directed to embodiments of the present invention, other and further embodiments of the invention may be devised without departing from the basic scope thereof and the scope thereof is determined by the claims that follow.

What is claimed is:

1. A method of minimizing alkylation catalyst regeneration comprising:
   substantially continuously feeding a first input stream comprising a reduced level of catalyst poisons and an alkylating agent to an alkylation system, contacting the first input stream and the alkylating agent with an alkylation catalyst to alkylate the first input stream and to form an output stream and removing the output stream from the alkylation system over a period of time substantially equal to a life of the alkylation catalyst, wherein the alkylation first input stream comprises a first aromatic compound and wherein the alkylation output comprises a second aromatic compound; and
   contacting a second input stream comprising a first level of catalyst poisons and the first aromatic compound with a cerium promoted zeolite catalyst in the presence of the alkylating agent to reduce the first level of catalyst poisons and form the first input stream having a reduced level of catalyst poisons prior to feeding the input stream to the alkylation system, wherein the reduced level of catalyst poisons is less than the first level of catalyst poisons and the life of the alkylation catalyst is longer than the same alkylation catalyst's life in the absence of contact with the cerium promoted zeolite catalyst.

2. The method of claim 1 further comprising regenerating the cerium promoted zeolite catalyst to a predetermined level to form a regenerated cerium promoted catalyst.

3. The method of claim 1, wherein the catalyst life of the cerium promoted zeolite catalyst is longer than a catalyst life of promoted zeolite beta catalysts modified with a rare earth metal ion other than cerium.

4. The method of claim 1, wherein the cerium promoted zeolite catalyst is regenerated more frequently than the alkylation catalyst.

5. The method of claim 1, wherein the cerium promoted zeolite catalyst retains substantially the same activity upon regeneration.

6. The method of claim 1, wherein the cerium promoted zeolite catalyst retains substantially the same selectivity upon regeneration as prior to regeneration.

7. The method of claim 1, wherein the amount of aluminum in the cerium promoted zeolite catalyst is directly related to the amount of cerium incorporated therein and the relationship thereof determines the activity and selectivity of the cerium promoted zeolite catalyst.

8. The method of claim 1, wherein the cerium promoted zeolite catalyst comprises a zeolite beta catalyst.

* * * * *